United States Patent [19]
Muraishi

[11] Patent Number: 5,154,889
[45] Date of Patent: Oct. 13, 1992

[54] CHEMICAL ANALYSIS APPARATUS

[75] Inventor: Katsuaki Muraishi, Kanagawa, Japan

[73] Assignee: Fuji Photo Film Co., Ltd., Kanagawa, Japan

[21] Appl. No.: 81,516

[22] Filed: Aug. 5, 1987

[30] Foreign Application Priority Data

Aug. 7, 1986 [JP] Japan ............... 61-185471
Aug. 8, 1986 [JP] Japan ............... 61-186184
Sep. 3, 1986 [JP] Japan ............... 61-207048

[51] Int. Cl.$^5$ .................................. G01N 21/00
[52] U.S. Cl. ............................ 422/65; 422/63; 422/67
[58] Field of Search ................ 422/63-67; 436/46

[56] References Cited

U.S. PATENT DOCUMENTS

| | | | |
|---|---|---|---|
| 4,224,032 | 9/1980 | Glover et al. | 422/65 |
| 4,636,360 | 1/1987 | Sakurada et al. | 422/67 |
| 4,670,219 | 6/1987 | Welson et al. | 422/64 |
| 4,676,952 | 6/1987 | Edelmann et al. | 422/64 |
| 4,708,886 | 11/1987 | Nelson | 422/64 |
| 4,855,109 | 8/1989 | Muraishi et al. | 436/46 |
| 4,857,272 | 8/1989 | Suguya | 422/65 |

Primary Examiner—Robert J. Warden
Assistant Examiner—Theresa A. Trembley
Attorney, Agent, or Firm—Sughrue, Mion, Zinn, Macpeak & Seas

[57] ABSTRACT

A chemical analysis apparatus is provided with an incubator having compartments for housing and incubating a chemical analysis slide having a reagent layer with a sample material applied thereon, and a read-out head moveable along the housing compartments to stand facing the reagent layer of the chemical analysis slide housed in the housing compartment via a read-out opening formed in the housing compartment, thereby to emit measuring light to the reagent layer and to measure an optical density of light reflected by the reagent layer. The chemical analysis apparatus comprises a temperature-controlled chamber for housing the incubator therein, a first temperature adjustment system provided with a heater and a temperature sensor secured to the incubator for maintaining the temperature in the housing compartment at a predetermined value, and a second temperature adjustment system provided with a heater disposed in the temperature-controlled chamber and a temperature sensor secured to the read-out head or disposed in the temperature-controlled chamber, thereby to maintain the temperature in the temperature-controlled chamber at the predetermined value.

6 Claims, 7 Drawing Sheets

CHEMICAL ANALYSIS APPARATUS

BACKGROUND OF THE INVENTION

1. Field of the Invention

This invention relates to a chemical analysis apparatus for applying a substance to be measured to a chemical analysis slide, i.e. a slide type chemical analysis device, provided with a reagent layer, maintaining the chemical analysis slide at a predetermined temperature (i.e. carrying out incubation) for a predetermined time, and then optically measuring the degree of color formation in the chemical analysis slide for quantitative analysis of the substance to be measured.

2. Description of the Prior Art

Quantitative analysis of a specific chemical constituent in a liquid sample is generally carried out for various industrial purposes. Particularly, it is very important in biochemical and clinical categories to quantitatively analyze chemical constituents or physical constituents in body fluid such as blood or urine.

In recent years, as disclosed in, for example, Japanese Patent Publication No. 53(1978)-21677 and Japanese Unexamined Patent Publication No. 55(1980)-164356, there has been developed and put into practice a dry type chemical analysis slide for quantitatively analyzing a specific chemical constituent or a specific physical constituent contained in a sample solution simply by applying a droplet of the sample solution. With the chemical analysis slide, it is possible to analyze a sample solution more simply and more quickly than when the conventional wet type analysis method is used. Therefore, the use of the chemical analysis slide is desirable particularly in medical organizations, research laboratories, or the like where many samples are to be analyzed.

In order to analyze a chemical constituent or the like contained in a sample solution by use of the chemical analysis slide, a measured amount of the sample solution is put on the chemical analysis slide and is maintained at a predetermined temperature (i.e. Incubated) for a predetermined time in an incubator to cause a color reaction, the chemical analysis slide is exposed to measuring light having a wavelength selected in advance in accordance with the combination of the substance to be measured with a reagent contained in the reagent layer of the chemical analysis slide, and the optical density of the light reflected by the chemical analysis slide is measured. In this manner, it is possible to achieve quantitative analysis of the substance to be measured such as the chemical constituents or the like.

Various chemical analysis apparatuses have heretofore been proposed for carrying out quantitative analysis of a substance to be measured in the manner as mentioned above. In general, the chemical analysis apparatus is provided with an incubator having a slide housing compartment for carrying out incubation. The temperature in the incubator is maintained at a predetermined value by a temperature adjustment means composed of a heater, a temperature sensor, a heater operation control circuit and the like. Also, in the case where the incubator is provided, the slide housing compartment is generally provided with a read-out opening, and a read-out head for emitting the measuring light to the reagent layer of the chemical analysis slide and measuring the optical density of the light reflected by the reagent layer is disposed to stand facing the reagent layer of the chemical analysis slide in the housing compartment via the read-out opening. In order to improve the efficiency of the quantitative analysis processing, there has also been proposed a chemical analysis apparatus wherein a plurality of the slide housing compartments are disposed side by side, and the read-out head is constituted for movement along the housing compartments.

However, with the chemical analysis apparatus provided with the incubator as mentioned above, air readily flows through the read-out opening formed in the slide housing compartment, and therefore the temperature in the slide housing compartment readily fluctuates in the course of incubation. As a result, the temperature of the chemical analysis slide fluctuates, and the predetermined conditions of incubation cannot be satisfied. Therefore, the accuracy of quantitative analysis is deteriorated.

One approach to elimination of the aforesaid problems is to house the incubator in a temperature-controlled chamber. However, the temperature-controlled chamber for housing a large incubator provided with a plurality of the slide housing compartments as mentioned above becomes large. In this case, even though the control is carried out for maintaining the temperature in the temperature-controlled chamber at a predetermined value, the temperature in the temperature-controlled chamber becomes uneven, the predetermined conditions of incubation cannot be satisfied at some positions in the temperature-controlled chamber, and therefore the accuracy of quantitative analysis is deteriorated.

SUMMARY OF THE INVENTION

The primary object of the present invention is to provide a chemical analysis apparatus wherein the temperature in a slide housing compartment of an incubator is accurately maintained at a predetermined value.

Another object of the present invention is to provide a chemical analysis apparatus wherein stabilization of the temperature of the external air in the vicinity of a read-out opening, decrease of the distance between a read-out head and a chemical analysis slide, increase in the heat capacity of an incubator, and prevention of adverse effects of external light on the read-out head are achieved simultaneously with a simple configuration.

The specific object of the present invention is to provide a chemical analysis apparatus which improves the accuracy of quantitative analysis.

The present invention provides a chemical analysis apparatus provided with an incubator having a plurality of housing compartments for respectively housing a chemical analysis slide having a reagent layer with a substance, which is to be measured, applied thereon, and for incubating the chemical analysis slide, and a read-out head moveable along said housing compartments to stand facing the reagent layer of the chemical analysis slide housed in one of said housing compartments via a read-out opening formed in each of the housing compartments, thereby to emit measuring light to the reagent layer and to measure the optical density of light reflected by the reagent layer, wherein the improvement comprises the provision of:
i) a temperature-controlled chamber for housing said incubator therein,
ii) a first temperature adjustment means provided with a heater and a temperature sensor secured to said incubator, thereby to maintain the temperature in each of said housing compartments at a predetermined value, and iii) a second temperature adjustment means provided with a heater disposed in said temperature-controlled chamber and a temperature sensor secured to said read-out head, thereby to maintain the temperature in said temperature-controlled chamber at said predetermined value.

The present invention also provides a chemical analysis apparatus provided with an incubator having at least one housing compartment for housing a chemical analysis slide having a reagent layer with a substance, which is to be measured, applied thereon, and for incubating the chemical analysis slide, and a read-out head disposed for standing face to face with the reagent layer of the chemical analysis slide housed in the housing compartment via a read-out opening formed in the housing compartment, thereby to emit measuring light to the reagent layer and to measure the optical density of light reflected by the reagent layer, wherein the improvement comprises the provision of:
i) a temperature-controlled chamber for housing said incubator therein,
ii) a first temperature adjustment means provided with a heater and a temperature sensor secured to said incubator, thereby to maintain the temperature in said housing compartment at a predetermined value, and
iii) a second temperature adjustment means provided with a heater and a temperature sensor disposed in said temperature-controlled chamber, thereby to maintain the temperature in said temperature-controlled chamber at said predetermined value.

With the first and second mentioned chemical analysis apparatuses in accordance with the present invention, the temperature in the temperature-controlled chamber is maintained at a predetermined value by the second temperature adjustment means, and there is no risk of a large difference in the temperature arising between the inside and the outside of the slide housing compartment. Therefore, even though air flows through the read-out opening of the slide housing compartment, the temperature in the housing compartment does not change or changes little, and any change in the temperature inside of the slide housing compartment can be quickly eliminated by the first temperature adjustment means. Since dual temperature adjustment is effected in the manner as mentioned above, the chemical analysis slide in the slide housing compartment can be accurately maintained at the predetermined temperature. Accordingly, it is possible to markedly improve the accuracy of quantitative analysis.

Also, with the first mentioned chemical analysis apparatus in accordance with the present invention wherein the temperature sensor of the second temperature adjustment means is secured to the moveable read-out head, the temperature in the temperature-controlled chamber can be detected over a wide area in the temperature-controlled chamber without using many temperature sensors. Therefore, even though a temperature gradient arises in the temperature-controlled chamber, it is possible to minimize the difference in the temperature between the inside and the outside of the slide housing compartment by controlling to maintain, for example, the mean temperature in the temperature-controlled chamber at the predetermined value. Accordingly, the accuracy of incubation and the accuracy of quantitative analysis can be improved markedly.

The present invention further provides a chemical analysis apparatus provided with an incubator for housing a plurality of chemical analysis slides therein and incubating them, and a read-out head moveable with respect to the chemical analysis slides housed in the incubator, thereby to emit measuring light to each of the chemical analysis slides and to measure the optical density of light reflected by the chemical analysis slide, wherein the improvement comprises the provision of:
i) a read-out head fitting recess into which a leading end portion of said read-out head is fitted, and which is formed in a slide supporting section of said incubator disposed between said chemical analysis slides housed in said incubator and said read-out head, said read-out head fitting recess being disposed on the read-out head side of said slide supporting section, and
ii) read-out openings for allowing passage of light therethrough with respect to said read-out head, said read-out openings being formed through said read-out head fitting recess at positions facing said chemical analysis slides housed in said incubator.

With the chemical analysis apparatus in accordance with the present invention mentioned last, the read-out head fitting recess is formed in the slide supporting section of the incubator, and the read-out openings are formed through the bottom portion of the read-out head fitting recess. Since the read-out head fitting recess acts to prevent air flow, air in the read-out head fitting recess stagnates therein, and the temperature of air therein does not readily change. Therefore, the temperature of external air in the vicinity of the read-out openings becomes stable.

Also, since the read-out head fitting recess is formed in the slide supporting section and the read-out head is fitted into the read-out head fitting recess, the thickness of the slide supporting section can be increased with the distance between the chemical analysis slide and the read-out head maintained small. Therefore, it is possible to maintain small the distance between the chemical analysis slide and the read-out head and, at the same time, to increase the heat capacity of the incubator.

Further, since the leading end portion of the read-out head is fitted into the read-out head fitting recess, the leading end portion of the read-out head is covered by the read-out head fitting recess, and it is possible to prevent external light from entering the read-out head and adversely affecting measurement carried out by the read-out head. As a result, measurement can be carried out very accurately by use of only a small amount of light.

BRIEF DESCRIPTION OF THE DRAWINGS

FIG. 5 is a perspective view of an example of the chemical analysis slide subjected to chemical analysis by use of the embodiment shown in FIG. 1.

DESCRIPTION OF THE PREFERRED EMBODIMENTS

The present invention will hereinbelow be described in further detail with reference to the accompanying drawings.

Figure 2:
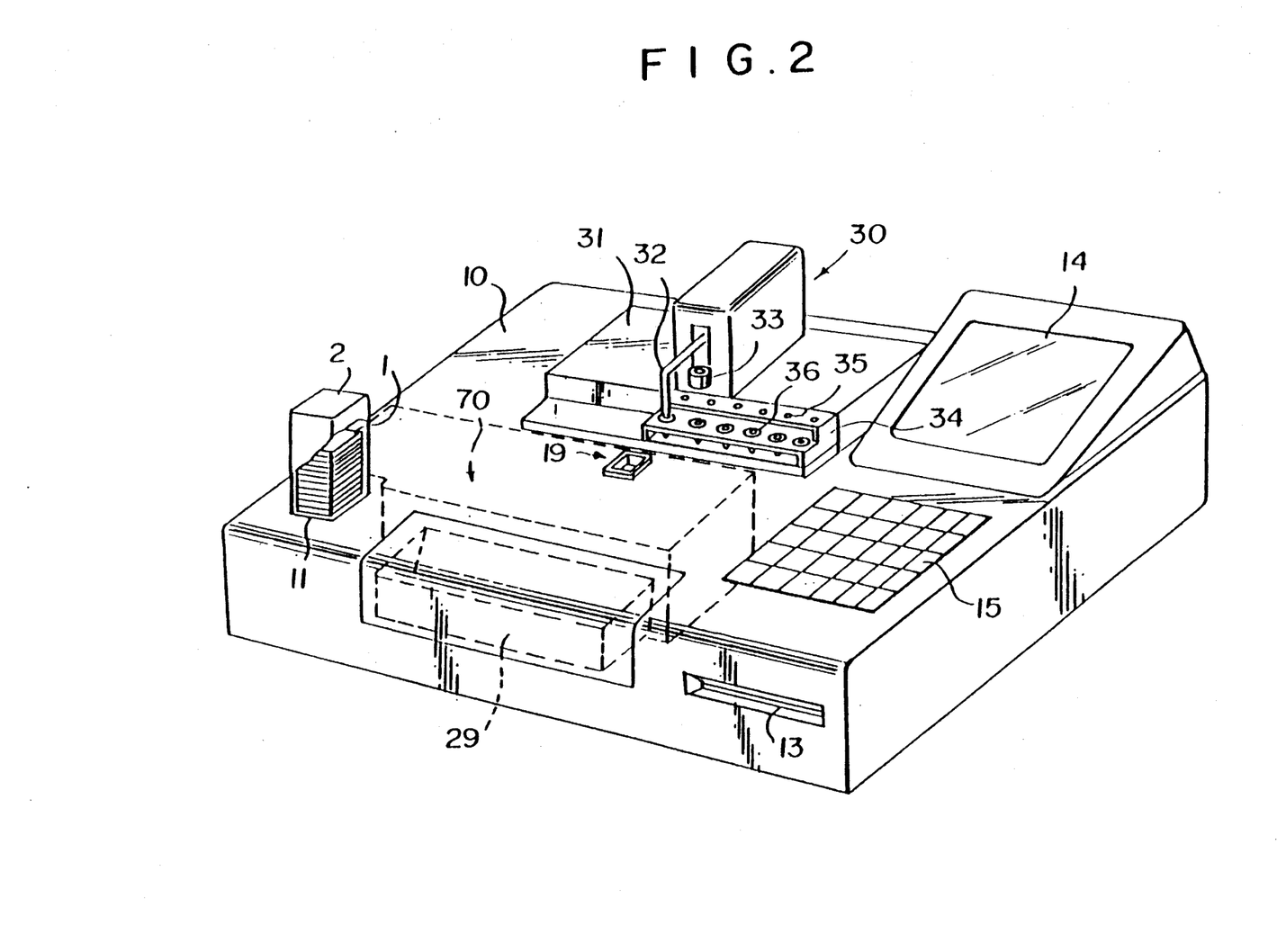
FIG. 2 is a general perspective view of the embodiment shown in FIG. 1, FIGS. 3 and 4 are a partially cutaway plan view and a partially cutaway front view of the embodiment shown in FIG. 1.
Figure 3:
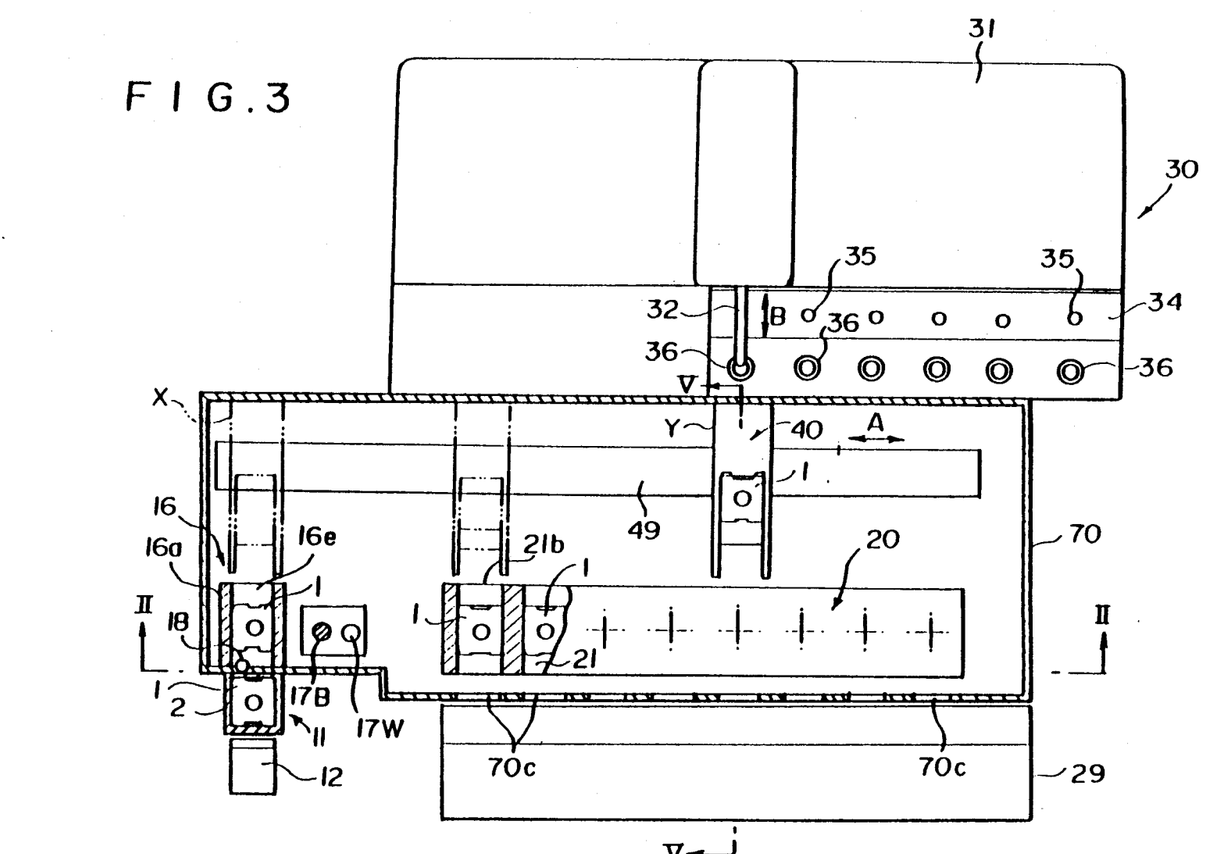
Figures 4, 5:
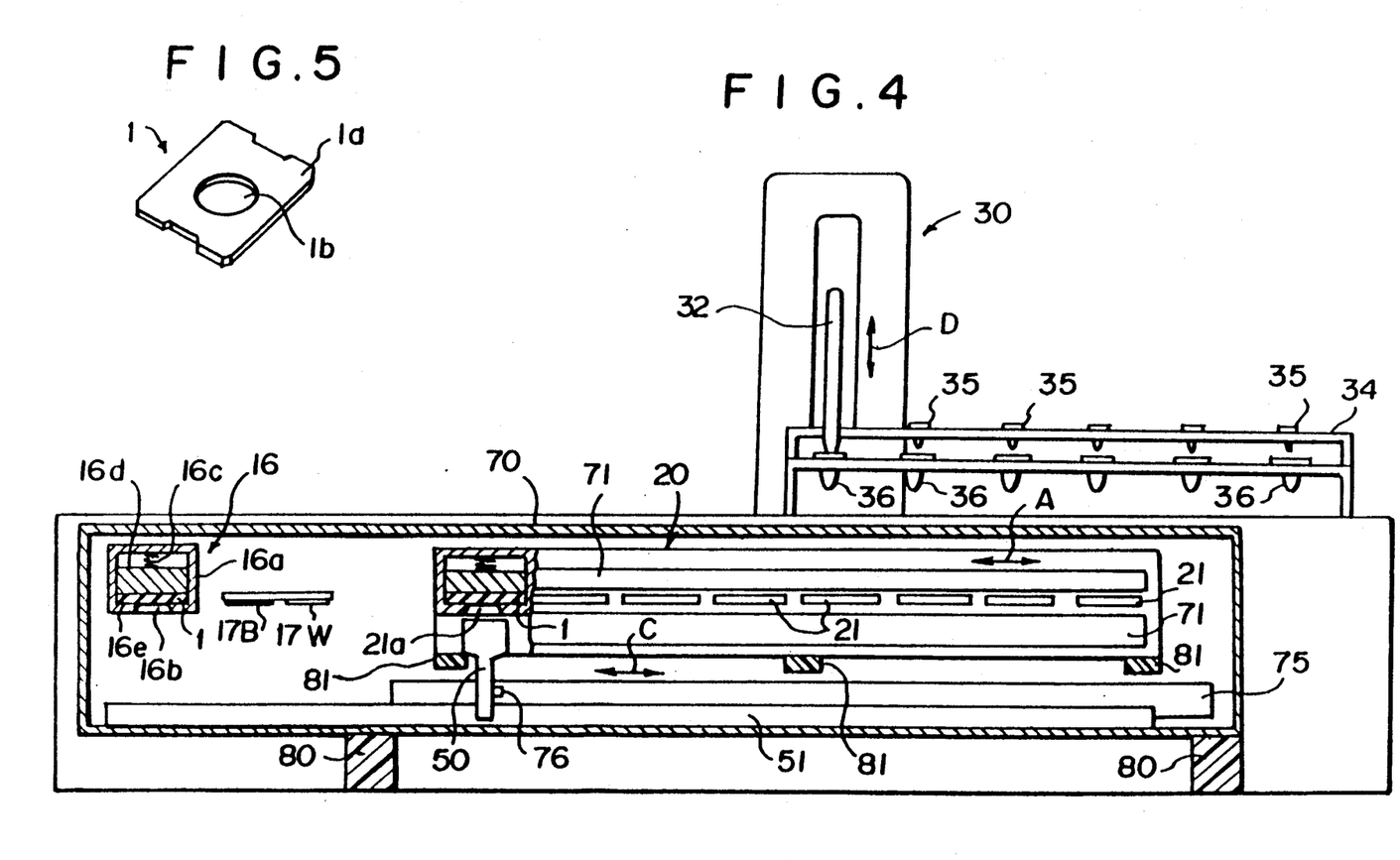

FIG. 2 shows the appearance of an embodiment of the chemical analysis apparatus in accordance with the present invention, FIG. 3 is a plan view of the major part of the embodiment shown in FIG. 2 with the case removed, and FIG. 4 is a front view taken along line II—II of FIG. 3. As shown, the chemical analysis apparatus is provided with a cartridge loading section 11 and a sample application device 30 disposed on a case 10, and an incubator 20, a slide feed-in and ejection means 40 and the like disposed inside of the case 10. Also, as shown in FIG. 2, this embodiment is provided with a display section 14 for displaying the measured values in the course of measurement or the like, an operating key section 15 for controlling the displaying of the measured values or the like, and a magnetic disk inserting section 13 for recording the measured values or the like on a magnetic disk, which are omitted for simplicity of explanation in FIGS. 3 and 4.

As shown in FIG. 2, a cartridge 2 inserted into the cartridge loading section 11 houses a plurality of unused chemical analysis slides 1, 1, ... stacked one upon another. As shown in FIG. 5, each of the chemical analysis slides 1, 1, ... loaded in the loading section 11 comprises a frame 1a having a circular hole for applying a spot of a liquid sample, and a dry type multi-layer film 1b disposed in the frame 1a and composed of a supporting material, a reagent layer, and a development layer, which are stacked in this sequence. A predetermined amount of the sample material (i.e. the substance to be measured) such as urine or blood is fed onto the film 1b, and incubated to cause a color reaction. As shown in FIG. 3, the chemical analysis slides 1, 1, ... in the cartridge 2 are pushed out by a pushing lever 12 one by one, starting from the lowest chemical analysis slide 1, to the fog measuring section 16. The fog measuring section 16 measures the reflected light density (fog density) of the film 1b of the chemical analysis slide 1 before the chemical analysis slide 1 is provided with the substance to be measured, and the measured fog density value is used for judging whether the chemical analysis slide 1 is acceptable or not and for correcting the measured density value of the chemical analysis slide 1, which is obtained after a color reaction, in accordance with the fog density. The fog measuring section 16 is composed of a frame 16a provided with a measuring opening 16b at the bottom section, and a retaining member 16d urged downwardly by a spring 16c in the frame 16a, and a housing compartment 16e for housing the chemical analysis slide 1 is formed between the upper surface of the bottom section of the frame 16a and the retaining member 16d. A bar code reading means 18 for reading a bar code (not shown) indicated on the chemical analysis slide 1 is disposed on the slide insertion side of the housing compartment 16e. A white reference plate 17W and a black reference plate 17B for measuring the density as a reference value for detecting the optical density of the light reflected by the chemical analysis slide 1 are disposed on the rightward lateral side of the fog measuring section 16.

Also, the incubator 20 is disposed on the rightward lateral side of the white reference plate 17W and the black reference plate 17B. A plurality of housing compartments 21, 21, ... for housing the chemical analysis slides 1, 1, ... are formed in the incubator 20 so that the chemical analysis slides 1, 1, ... stand side by side in a line on the same plane as the chemical analysis slide 1 in the fog measuring section 16. The incubator 20 is housed in a temperature-controlled chamber 70. A receiving member 29 for receiving the used chemical analysis slides 1, 1, ... ejected from the housing compartments 21, 21, ... is disposed in front of the temperature-controlled chamber 70. Further, as shown in FIG. 4, a read-out head 50 slideable in the transverse direction as indicated by the arrow C to face the lower surface of the incubator 20 is disposed below the incubator 20. The read-out head 50 is combined with a rail 51 secured to an upper surface of a bottom plate of the temperature-controlled chamber 70, and moved in the aforesaid direction by being operated by a drive means (not shown), for example, a linear motor. The rail 51 extends up to the position below the fog measuring section 16, and therefore the read-out head 50 can be moved up to the fog measuring section 16 to face the chemical analysis slide 1 at the fog measuring section 16.

Figure 1:
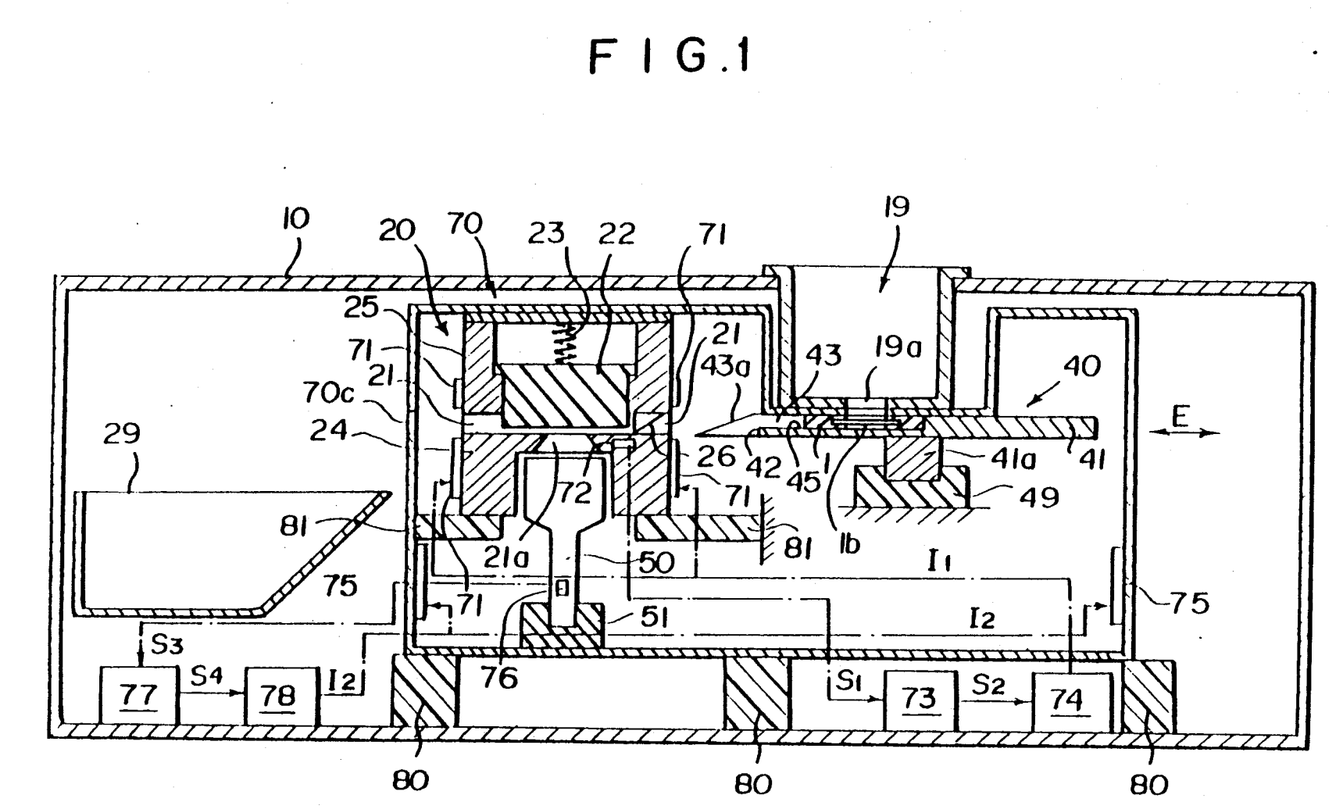
FIG. 1 is a sectional side view showing the major part of an embodiment of the chemical analysis apparatus in accordance with the present invention.

As shown in detail in FIG. 1 which is a sectional view taken along line V—V of FIG. 3, a plurality of first heaters 71, 71, ... are secured to the incubator 20 along the respective housing compartments 21, 21, .... Also, a first temperature sensor 72 is disposed at a position close to the housing compartment 21 inside of the incubator 20. A temperature detection signal S1 generated by the first temperature sensor 72 is sent to a first control circuit 73, which generates a temperature control signal S2 in accordance with a deviation between the measured temperature represented by the temperature detection signal S1 and a predetermined setting temperature T. The temperature control signal S2 is sent to a heater operating circuit 74 for supplying heating current I1 to the first heaters 71, 71, ..., and the heater operating circuit 74 turns on and off the heating current I1 or changes the level of the heating current I1 on the basis of the temperature control signal S2, thereby to maintain the temperatures in the housing compartments 21, 21, ... at the predetermined setting temperature T. On the other hand, second heaters 75, 75 for heating air in the temperature-controlled chamber 70 are disposed in the temperature-controlled chamber 70, and a second temperature sensor 76 for detecting the temperature in the temperature-controlled chamber 70 is secured to the read-out head 50. A temperature detection signal S3 generated by the second temperature sensor 76 is fed to a second control circuit 77, and a temperature control signal S4 corresponding to the temperature detection signal S3 is sent to a heater operating circuit 78 for controlling a heating current I2. In this manner, the temperature in the temperature-controlled chamber 70 is maintained at the aforesaid predetermined temperature T. In this embodiment, the temperature detection signal S3 is sampled each time the read-out head 50 is stopped at the position facing each of the housing compartments 21, 21, .... A mean value of eight sampled signals S3, S3, ... (equal to the number of the housing compartments 21, 21, ...), i.e. the signal S3 sampled in this manner plus seven signals S3, S3, ... sampled previously and stored in a memory, is calculated. Temperature control is effected so that the mean temperature represented by the mean value calculated in this manner coincides with the aforesaid predetermined temperature T. (Each time the mean value is calculated, the signal S3 which is oldest in the sampling sequence is deleted from the memory.) In the case where the temperature control is carried out in this manner, the total of differences in the temperature between the inside and the outside of the respective housing compartments 21, 21, ... can be minimized when a temperature gradient arises in the temperature-controlled chamber 70. Specifically, it is possible to prevent the problem that, though the differences in the temperature between the inside and the outside of some housing compartments 21, 21, ... may be very small, the differences in the temperature between the inside and the outside of other housing compartments 21, 21, ... become markedly large.

The temperature-controlled chamber 70 is secured to the bottom surface of the case 10 via heat insulating materials 80, 80, .... Also, the incubator 20 is supported in the temperature-controlled chamber 70 via heat insulating materials 81, 81, ....

The chemical analysis slide 1 housed in the incubator 20 is subjected to a color reaction between the sample material applied to the film 1b of the chemical analysis slide 1 and the reagent of the film 1b, and the extent of the color reaction is optically measured by the read-out head 50 via a read-out opening 21a formed in the lower surface of each housing compartment 21. At the incubator 20, in order to cause the color reaction of the sample such as urine or blood, it is necessary to maintain the chemical analysis slides 1, 1, ... at a temperature approximately equal to the body temperature (37° C.).

On the other hand, the slide feed-in and ejection means 40 moveable in the transverse direction as indicated by the arrow A to face one of inlet openings 21b, 21b, ... of the housing compartments 21, 21, ... is disposed at the rear of the incubator 20. The slide feed-in and ejection means 40 is combined with a rail 49 secured in the temperature-controlled chamber 70 and moved by a drive means (not shown) such as a linear motor in the aforesaid direction. The slide feed-in and ejection means 40 is moveable up to a position facing the fog measuring section 16 (the position as indicated by the chain line X in FIG. 3) besides the position facing the incubator 20. Therefore, the chemical analysis slide 1 pushed by the pushing lever 12 out of the fog measuring section 16 can be received by the slide feed-in and ejection means 40 moving to the position as indicated by the chain line X. The slide feed-in and ejection means 40 is moveable in the direction as indicated by the arrow A in the temperature-controlled chamber 70.

The sample application device 30 is disposed at the rear of the slide feed-in and ejection means 40. The sample application device 30 is provided with a sample base 34 moveable in the transverse direction as indicated by the arrow A on a base plate 31, and holding thereon sample tubes 36, 36, ... and application tips 35, 35, ... disposed in two lines in the transverse direction. A pipette 32 of the sample application device 30 is moveable vertically as indicated by the arrow D and forwardly and backwardly as indicated by the arrow B with respect to the base plate 31. The pipette 32 is moved vertically, forwardly and backwardly to fit one of the application tips 35, 35, ... to the lower end of the pipette 32, to draw a predetermined amount of the substance to be measured from one of the sample tubes 36, 36, ... into the application tip 35 by suction, and then to feed the substance to be measured onto the film 1b of the chemical analysis slide 1 on the slide feed-in and ejection means 40 at a sample applying section 19. At this time, the application tips 35, 35, ... are exchanged for the respective sample tubes 36, 36, ... so that the substances to be measured which are contained in the sample tubes 36, 36, ... are not mixed with each other.

The chemical analysis slide 1 with the substance to be measured applied thereon is fed by the slide feed-in and ejection means 40 into the predetermined housing compartment 21. The slide holding configurations of the slide feed-in and ejection means 40 and the incubator 20 will hereinbelow be described in detail with reference to FIG. 1. The slide feed-in and ejection means 40 is composed of a supporting block 41a moveable in the transverse direction as indicated by the arrow A along the rail 49, and a supporting plate 41 disposed on the supporting block 41a. The supporting plate 41 is constituted by a holding portion 45 for receiving the chemical analysis slide 1 thereon, step-like portions 43, 43 formed at both ends of the holding portion 45, a pair of wedge-like insert portions 43a, 43a which are formed at the leading ends of the step-like portions 43, 43, and a slide ejecting protrusion 42 formed at the leading end of the holding portion 45. When the slide feed-in and ejection means 40 is moved in the transverse direction along the rail 49 up to the position Y as indicated in FIG. 3, the film 1b of the chemical analysis slide 1 held at the holding section 45 stands facing an opening 19a of the sample applying section 19, and the substance to be measured is applied from the pipette 32 of the sample application device 30 onto the film 1b via the opening 19a. Then, the slide feed-in and ejection means 40 is moved along the rail 49 up to the position facing the housing compartment 21 which is to house the chemical analysis slide 1. The supporting plate 41 is slideable on the supporting block 41a forwardly and backwardly as indicated by the arrow E, and the chemical analysis slide 1 held on the supporting plate 41 is fed into the housing compartment 21 of the incubator 20 by the movement of the supporting plate 41.

The incubator 20 is composed of a supporting member 24 for supporting the chemical analysis slide 1 fed into the incubator 20 and having a read-out opening 21a, a pushing member 22 facing the supporting member 24 and moveable vertically, a spring 23 for urging the pushing member 22 downwardly, a main body member 25 for moveably supporting the pushing member 22, and a leaf-spring stop 26 secured to the inlet opening 21a of the housing compartment 21.

The operations of the slide feed-in and ejection means 40 and the incubator 20 in the case where the chemical analysis slide 1 on which read-out by the read-out head 50 has been finished is housed and held in the housing compartment 21 and is to be replaced by a new chemical analysis slide 1 on the slide feed-in and ejection means 40 will be described below. The chemical analysis slide 1 in the housing compartment 21 is gripped between the supporting member 24 and the pushing member 22 by the urging force of the spring 23. Therefore, when the supporting plate 41 is moved forwardly, i.e. leftwardly in FIG. 1, the wedge-like insert portion 43a first comes between the pushing member 22 and the supporting member 24, and pushes the pushing member 22 up to release the gripping of the chemical analysis slide 1. Then, the slide ejecting protrusion 42 comes into contact with the rear end of the chemical analysis slide 1 in the housing compartment 21, pushes the chemical analysis slide 1 forwardly, and ultimately ejects the chemical analysis slide 1 out of the housing compartment 21 into the receiving member 29 via an opening 70c of the temperature-controlled chamber 70. At this time, the new chemical analysis slide 1 held at the holding portion 45 of the supporting plate 41 is disposed at a predetermined position in the housing compartment 21, and the leaf-spring stop 26 enters a pair of recesses (not shown) formed in the rear end portion of the holding portion 45 of the supporting plate 41. Thereafter, the supporting plate 41 is returned backwardly. At this time, since the leaf-spring stop 26 contacts the rear end face of the chemical analysis slide 1 and prevents the chemical analysis slide 1 from moving, the supporting plate 41 alone is returned backwardly and, as a result, the chemical analysis slide 1 is gripped between the supporting member 24 and the pushing member 22 in the housing compartment 21.

The operations of the aforesaid embodiment will be described hereinbelow. First, the lowest chemical analysis slide 1 among the chemical analysis slides 1, 1, ... stacked in the cartridge 2 loaded in the cartridge loading section 11 is pushed out by the pushing lever 12, and housed in the housing compartment 16e at the fog measuring section 16. At this time, the bar code of the chemical analysis slide 1 is read by the bar code reading means 18. Thereafter, the read-out head 50 is moved to the position facing the measurement opening 16b of the fog measuring section 16, and fog measurement is carried out on the chemical analysis slide 1 before it is provided with the substance to be measured. When the read-out head 50 is moved, it stands facing the white reference plate 17W and the black reference plate 17B, and measures the optical density values of the light reflected thereby. The results of the measurement are utilized as reference densities in measurement of the optical density of the light reflected by the chemical analysis slide 1.

After the fog measurement is conducted, the chemical analysis slide 1 is pushed by the pushing lever 12 out of the fog measuring section onto the holding portion 45 of the slide feed-in and ejection means 40 moved to the position as indicated by the chain line X in FIG. 3.

Then, the slide feed-in and ejection means 40 is moved rightwardly along the rail 49 up to the position as indicated by the full line Y in FIG. 3 facing the pipette 32 of the sample application device 30. At this position, the substance to be measured which is contained in the sample tube 36 is fed by the pipette 32 onto the film 1b of the chemical analysis slide 1 held on the slide feed-in and ejection means 40.

Thereafter, the slide feed-in and ejection means 40 is moved along the rail 49 in the transverse direction as indicated by the arrow A to the position facing the predetermined housing compartment 21 of the incubator 20. Then, the chemical analysis slide 1 is fed into the housing compartment 21 in the manner as mentioned above. As mentioned above, the temperature in the housing compartment 21 of the incubator 20 is maintained at the predetermined temperature T by the first heaters 71, 71, ..., the first temperature sensor 72, the first control circuit 73 and the heater operating circuit 74. Therefore, the chemical analysis slide 1 housed in the housing compartment 21 is incubated at the predetermined temperature T. After the chemical analysis slide 1 is incubated in the incubator 20, measuring light is emitted by the read-out head 50, which has been moved to the position below the housing compartment 21, to the chemical analysis slide 1 via the read-out opening 21a, and the amount of the light reflected by the chemical analysis slide 1 is measured by the read-out head 50. In this manner, the optical density of the light reflected by the film 1b of the chemical analysis slide 1 is measured, and the substance to be measured which has been applied onto the film 1b is analyzed quantitatively. When the measurement is finished, the chemical analysis slide 1 is ejected from the housing compartment 21 into the receiving member 29 by the slide feed-in and ejection means 40. It is possible to carry out chemical analysis automatically and continuously by using many chemical analysis slides and repeating the aforesaid operations.

Since the housing compartment 21 of the incubator 20 is provided with the read-out opening 21a, air outside of the housing compartment 21 will readily flow into the housing compartment 21 through the read-out opening 21a. In the case where air flows in this manner, the temperature in the housing compartment 21 readily fluctuates even though it is controlled by the temperature adjustment means composed of the first heaters 71, 71, ..., the first temperature sensor 72, the first control circuit 73 and the heater operating circuit 74. However, with this embodiment, since the whole incubator 20 is housed in the temperature-controlled chamber 70 and the air temperature (the aforesaid means temperature) in the temperature-controlled chamber 70 is controlled at the predetermined temperature T, little difference in the temperature arises between the inside and the outside of the housing compartment 21. Therefore, even though air flows through the read-out opening 21a of the housing compartment 21, the temperature in the housing compartment 21 does not change or changes little, and any change in the temperature inside of the housing compartment 21 can be eliminated quickly. That is, the temperature of the chemical analysis slide 1 in the housing compartment 21 can be accurately maintained at the predetermined temperature T.

For example, in the case where the time for which the read-out head 50 is maintained stationary at the position facing the housing compartment 21 is comparatively long, instead of controlling so that the aforesaid mean temperature coincides with the predetermined temperature T, the temperature control may be carried out so that the air temperature in the temperature-controlled chamber 70 at each stopping position of the read-out head 50 coincides with the predetermined temperature T.

Also, in this embodiment wherein the incubator 20 is held in the temperature-controlled chamber 70 via the heat insulating materials 81, 81, ... and the temperature-controlled chamber 70 is secured to the case 10 of the apparatus via the heat insulating materials 80, 80, ..., heat cannot readily escape from the holding sections of the incubator 20 and the temperature-controlled chamber 70 to the exterior. Therefore, it is possible to efficiently prevent the problem that the temperatures of the housing compartments 21, 21, ... in the vicinity of the holding sections become lower than the temperatures of the other housing compartments 21, 21, ....

In the aforesaid embodiment, the slide feed-in and ejection means 40 is also housed in the temperature-controlled chamber 70. However, the size of the temperature-controlled chamber 70 may be decreased so that only the incubator 20 can be housed therein. In this case, the temperature-controlled chamber 70 may be provided with a small opening through which the leading end portion of the slide feed-in and ejection means 40 is to be passed. However, also the slide feed-in and ejection means 40 should preferably be housed in the temperature-controlled chamber 70 as in the aforesaid embodiment since the chemical analysis slide 1 is preheated before it is fed into the housing compartment 21 and any fluctuation in the temperature in the housing compartment 21 can be prevented more reliably. This applies not only to the housing compartment 21 into which the chemical analysis slide 1 is fed, but also to the housing compartments 21, 21 adjacent to said housing compartment 21. That is, it becomes possible to prevent the problem that the temperature of the chemical analysis slide 1 incubated in the housing compartment 21 is caused to become low by feeding-in of a new cold chemical analysis slide 1 into the housing compartment 21 adjacent to said housing compartment 21. Also, since the temperature-controlled chamber 70 is supported via the heat insulating materials 80, 80, ... as mentioned above, it is not always possible to accurately align the incubator 20 disposed in the temperature-controlled chamber 70 with the slide feed-in and ejection means 40 disposed outside of the temperature-controlled chamber 70. However, in the case where the slide feed-in and ejection means 40 is also housed in the temperature-controlled chamber 70 besides the incubator 20 as in the aforesaid embodiment, the problem with regard to the alignment does not arise, and feeding-in of the chemical analysis slide 1 can be achieved reliably.

Also, in the aforesaid embodiment, the chemical analyisis slides 1, 1, ... are disposed side by side in a line inside of the incubator 20, and the read-out head 50 is moved to measure the optical density of the light reflected by each chemical analysis slide 1. However, the present invention is applicable also to a chemical analysis apparatus provided with a read-out section having a difference configuration, for example, a chemical analysis apparatus wherein a rotatable turret feeds the chemical analysis slides sequentially into a fixed read-out section, or a chemical analysis apparatus wherein the chemical analysis slides are fed one after another into an incubator provided with a single housing compartment. Also, a plurality of the first temperature sensors 72, 72, ... may be disposed at appropriate positions, and a mean value of the outputs of the respective first temperature sensors 72, 72, ... may be calculated for detecting the temperature in the housing compartment 21.

Further, instead of automatically applying the substance to be measured by the sample application device 30 at the sample applying section 19, the substance to be measured may be manually applied by use of a micropipette or the like.

Figure 6:
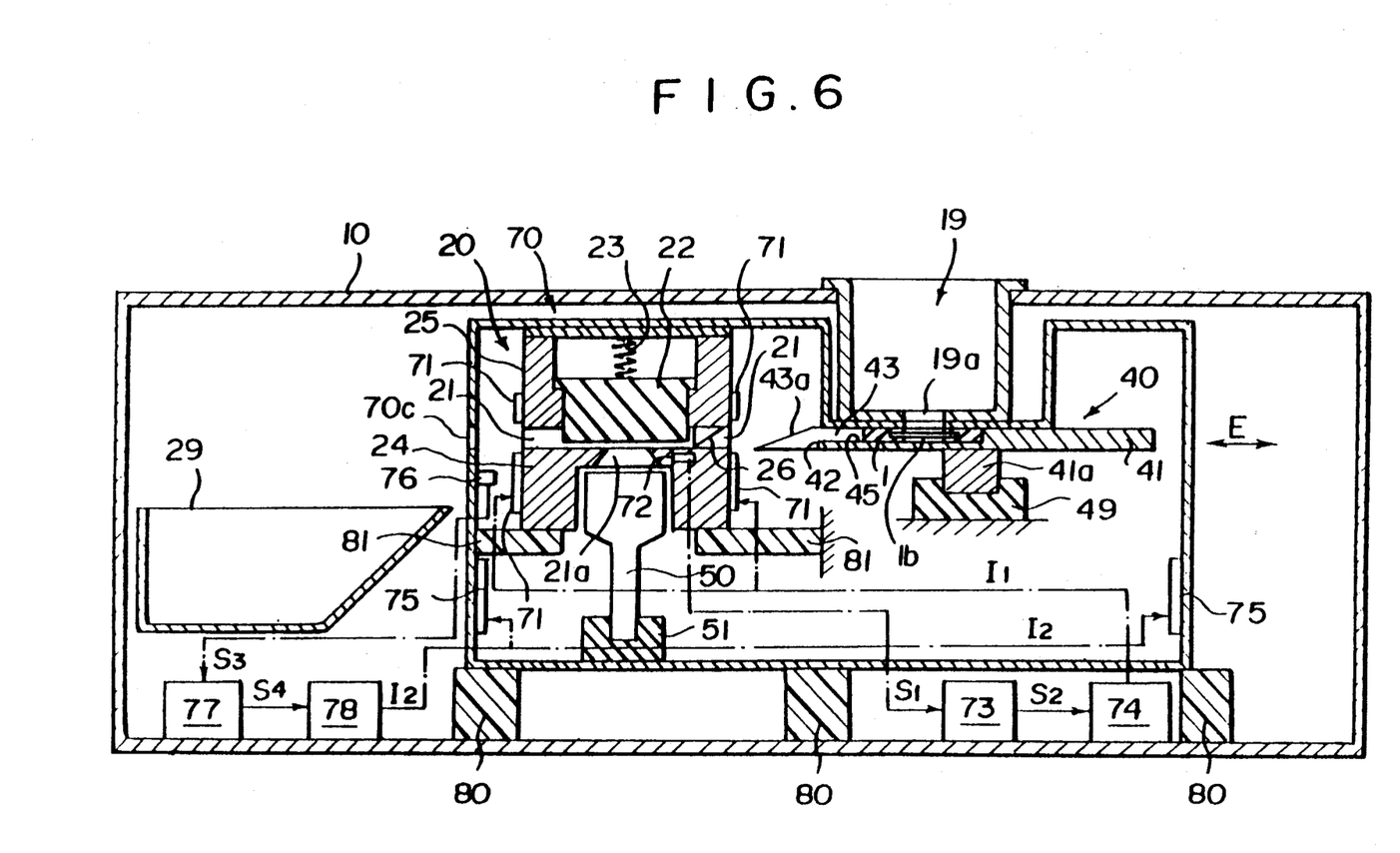
FIG. 6 is a sectional side view of the major part of another embodiment of the chemical analysis apparatus in accordance with the present invention.

Another embodiment of the chemical analysis apparatus in accordance with the present invention will now be described with reference to FIG. 6. FIG. 6 shows the cross-sectional configuration of the chemical analysis apparatus shown in FIG. 2, taken along the line V—V of FIG. 3. In FIG. 6, similar elements are numbered with the same reference numerals with respect to FIG. 1.

The embodiment shown in FIG. 6 has the same configuration as the embodiment shown in FIG. 1, except that the second temperature sensor 76 constituting the second temperature adjustment means together with the second heaters 75, 75, ... is disposed in the temperature-controlled chamber 70 at the position shown in FIG. 6, instead of being secured to the read-out head 50 as shown in FIG. 1. Also in this embodiment, the same affects as with the embodiment shown in FIG. 1 can be obtained. In this embodiment, a plurality of the first temperature sensors 72, 72, ... and a plurality of the second temperature sensors 76, 76, ... may be disposed at appropriate positions, and a mean value of the outputs of the respective first temperature sensors 72, 72, ... and a mean value of the outputs of the respective second temperature sensors may be calculated for detecting the temperature in the housing compartment 21 and the temperature in the temperature-controlled chamber 70.

A further embodiment of the chemical analysis apparatus in accordance with the present invention will hereinbelow be described with reference to FIGS. 7, 8 and 9.

Figure 7:
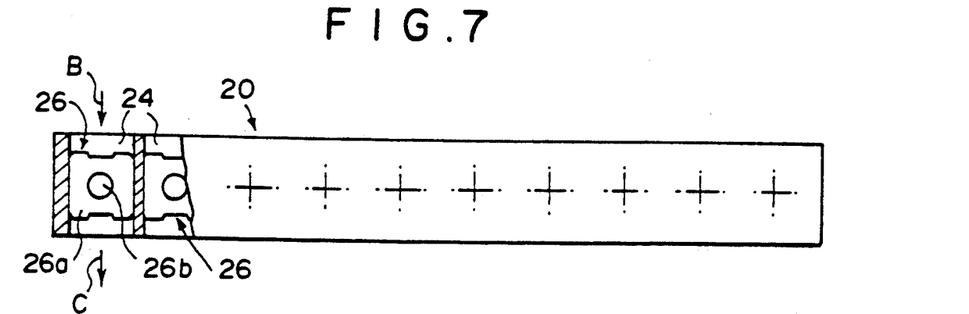
FIG. 7 is a partially cutaway schematic plan view of the major part of a further embodiment of the chemical analysis apparatus in accordance with the present invention.
Figure 8:
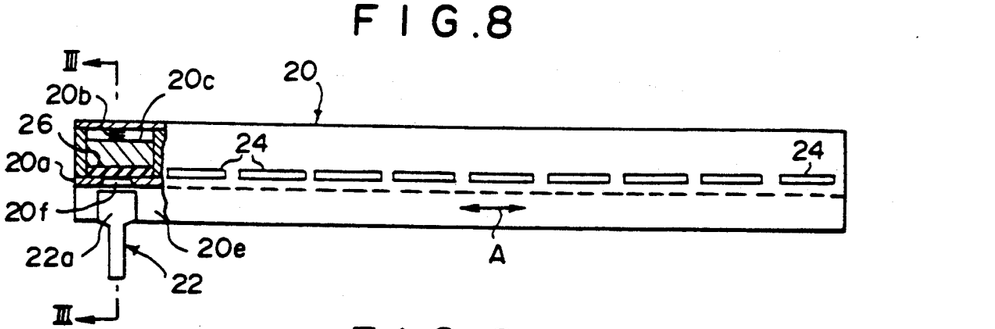
FIG. 8 is a partially cutaway schematic side view of the embodiment of FIG. 7.
Figure 9:
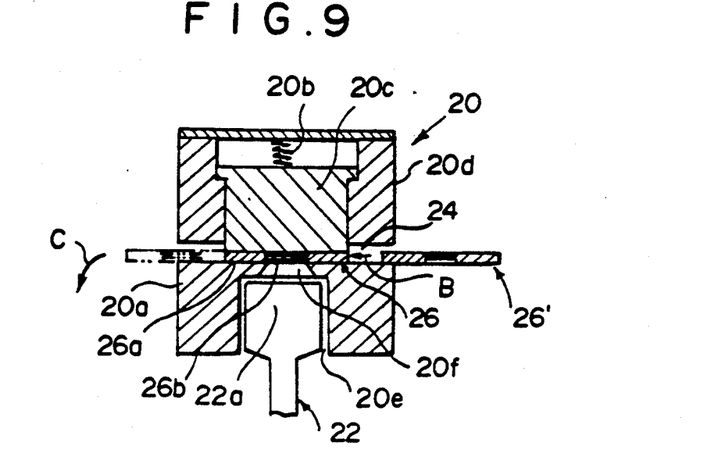
FIG. 9 is a sectional view taken along line III—III of FIG. 8.

As shown in FIGS. 7, 8 and 9, this embodiment is provided with an incubator 20 and a read-out head 22. The incubator 20 is provided with ten housing compartments 24, 24, ... disposed side by side in a line on the same plane in the incubator 20. The housing compartments 24, 24, ... house and incubate chemical analysis slides 26, 26, ... one by one. The incubator 20 is provided with a heater (not shown) for adjusting the temperature in each housing compartment 24 when necessary and maintaining the temperature constant for incubating the chemical analysis slide 26. The read-out head 22 is disposed below the incubator 20 for emitting measuring light to the chemical analysis slide 26 in each housing compartment 24 from below and measuring the optical density of the light reflected by the chemical analysis slide 26. The read-out head 22 is moved below the incubator 20 by a linear motor or the like along a rail (not shown) extending in the longitudinal direction of the incubator 20 as indicated by the arrow A along the array of the housing compartments 24, 24, ..., and is positioned exactly below each housing compartment 24.

Each of the chemical analysis slides 26, 26, ... comprises a frame 26a having a circular hole for applying spots of a liquid sample, and a dry type multi-layer film 26b disposed in the frame 26a and composed of a supporting material, a reagent layer, and a development layer, which are stacked in this sequence. A predetermined amount of the sample material (i.e. the substance to be measured) such as urine or blood is fed onto the film 26b, and incubated to cause a color reaction.

In more detail, the incubator 20 is composed of a slide supporting section 20a for supporting the chemical analysis slide 26 fed into the housing compartment 24, a vertically moveable pushing member 20c facing the slide supporting section 20a and urged by a spring 20b downwardly, and a main body member 20d for moveably supporting the pushing member 20c. The slide housing compartment 24 is formed between the slide supporting section 20a and the main body member 20d.

A read-out head fitting recess 20e into which a leading end portion 22a of the read-out head 22 is fitted is formed on the lower side, i.e. on the read-out head side, of the slide supporting section 20a. The read-out head fitting recess 20e is shaped in a linear groove form extending along the array of the housing compartments 24, 24, ... so that the leading end portion 22a of the read-out head 22 can move along the rail up to the position exactly below each housing compartment 24.

Also, a read-out opening 20f is formed through the read-out head fitting recess 20e at the position facing each housing compartment 24 so that light can pass through the read-out opening 20f between the chemical analysis slide 26 housed in the housing compartment 24 (particularly, the multi-layer film 26b of the chemical analysis slide 26 housed at the predetermined position on the slide supporting section 20a) and the read-out head 22. The read-out opening 20f should preferably be shaped in a trapezoidal cross-sectional form so that the light reflected by the chemical analysis slide 26 can be detected efficiently. With the configuration as mentioned above, the chemical analysis slide 26 is fed to the predetermined position on the slide supporting section 20a of the incubator 20, and is incubated in the condition pushed by the pushing member 20c. The read-out head 22 in the condition fitted into the read-out head fitting recess 20e of the slide supporting section 20a emits light to the chemical analysis slide 26 via the read-out opening 20f and measures the optical density of the light reflected by the chemical analysis slide 26.

As shown in FIG. 9 for example, feeding of a new chemical analysis slide 26' with the sample solution applied thereon into the housing compartment 24 and ejection of the old chemical analysis slide 26 from the housing compartment 24 after measurement may be carried out by pushing the new chemical analysis slide 26' in the direction as indicated by the arrow B, and pushing and ejecting the old chemical analysis slide 26 by the new chemical analysis slide 26' in the direction as indicated by the arrow C.

In the embodiment mentioned above with reference to FIGS. 7, 8 and 9, the incubator 20 is fixed and the read-out head 22 is moveable. Instead, the read-out head 22 may be fixed and the incubator 20 may be formed for movement.

Figure 10:
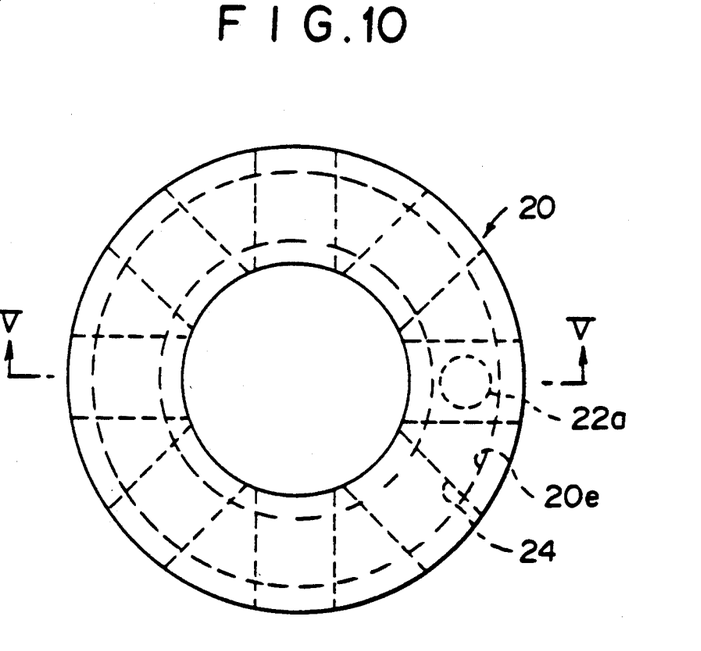
FIG. 10 is a schematic plan view of the major part of a still further embodiment of the chemical analysis apparatus in accordance with the present invention.
Figure 11:
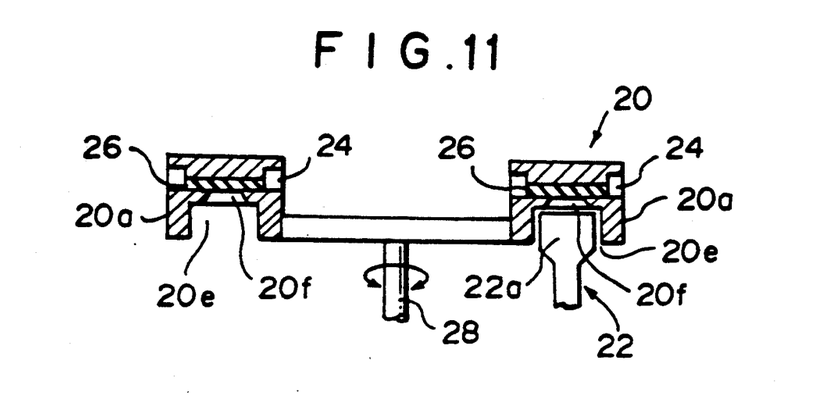
FIG. 11 is a sectional view taken along line V—V of FIG. 10.

Besides the chemical analysis apparatus wherein the read-out head 22 is moved linearly with respect to the incubator 20 in the manner as mentioned above, the present invention is also applicable to a chemical analysis apparatus wherein either one of the read-out head and the incubator is moved along a circular path with respect to the other. An embodiment of such a type will hereinbelow be described with reference to FIGS. 10 and 11. This embodiment is provided with a circular ring-like incubator 20 having twelve housing compartments 24, 24, ... disposed at equal intervals on the same circumference. The read-out head 22 is fixed at the predetermined position as shown below the incubator 20. The incubator 20 is rotated at intervals of a predetermined angle (45° in this embodiment) around a rotation shaft 28, thereby to dispose each housing compartment 24 above the read-out head 22. The read-out head fitting recess 20e is formed in the lower surface of the slide supporting section 20a of the incubator 20. The read-out head fitting recess 20e is shaped in a circular groove form along the array of the housing compartments 24, 24, ... so that the incubator 20 can be rotated with the leading end portion 22a of the read-out head 22 fitted into the read-out head fitting recess 20e from below. The leading end portion 22a of the read-out head 22 is fitted into the read-out head fitting recess 20e. Also, the slide supporting section 20a is provided with the read-out opening 20f formed for each of the housing compartments 24, 24, ... so that the read-out opening 20f is opened downwardly and communicates with the inside of the read-out head fitting recess 20e. Also in this embodiment, the incubator 20 may be fixed, and the read-out head 22 may be formed moveably along the read-out head fitting recess 20e.

In the embodiments as mentioned above with reference to FIGS. 7 to 11, the read-out opening for allowing passage of light between the chemical analysis slide housed in the housing compartment and the read-out head is formed in the slide supporting section of the incubator disposed between the chemical analysis slide housed in the housing compartment and the read-out head. Also, the read-out head fitting recess having the bottom portion in which an end face portion of the read-out opening is opened is formed in the surface of the slide supporting section on the read-out head side, and the leading end portion of the read-out head is fitted into the read-out head fitting recess.

Since the read-out head fitting recess is formed and the read-out head is fitted into the read-out head fitting recess, even though the thickness of the slide supporting section of the incubator is made large to increase the heat capacity of the incubator, the distance between the chemical analysis slide and the read-out head can be maintained small. Thus decrease in said distance and increase in the heat capacity of the incubator can be achieved simultaneously.

Also, air in the read-out head fitting recess stays in the read-out head fitting recess, and little air flows into and out of the read-out head fitting recess. Therefore, the temperature of external air in the vicinity of the read-out opening can be stabilized.

Also, since the read-out head is covered by the read-out head fitting recess, there is no risk of the read-out head being adversely affected by external light.

The chemical analysis apparatus in accordance with the present invention is not limited to the embodiments as mentioned above with reference to FIGS. 7 to 11 and may be modified in various manners. Also, the chemical analysis apparatus in accordance with the present invention may be provided with a sample application means, a slide feed-in and ejection means, and various other means besides the incubator and the read-out head.

I claim:

1. A chemical analysis apparatus provided with an incubator having a plurality of housing compartments for respectively housing a chemical analysis slide having a reagent layer with a substance, which is to be measured, applied thereon, and for incubating the chemical analysis slide, and a read-out head moveable along said housing compartments to stand facing the reagent layer of the chemical analysis slide housed in one of said housing compartments via a read-out opening formed in each of the housing compartments, thereby to emit measuring light to the reagent layer and to measure optical density of light reflected by the reagent layer, wherein the improvement comprises the provision of:
i) a temperature-controlled chamber for housing said incubator therein,
ii) a first temperature adjustment means provided with a heater and a temperature sensor secured to said incubator, thereby to maintain the temperature in each of said housing compartments at a predetermined value,
iii) a second temperature adjustment means provided with a heater disposed in said temperature-controlled chamber and a temperature sensor secured to said read-out head, said temperature sensor generating a temperature detection signal, thereby to maintain the temperature in said temperature-controlled chamber at said predetermined value, and further comprising means for calculating a mean value of a plurality of sampled temperature detection signals equal in number to said plurality of housing compartments, such that temperature control is effected so that a mean temperature represented by said mean value coincides with said predetermined value.

2. An apparatus as defined in claim 1 wherein said temperature-controlled chamber is supported in a main body of said chemical analysis apparatus via heat insulating materials, and said incubator is supported in said temperature-controlled chamber via heat insulating materials.

3. An apparatus as defined in claim 1 wherein a slide conveyance system for feeding said chemical analysis slide into said housing compartment is accommodated in said temperature-controlled chamber.

4. An apparatus as defined in claim 1 wherein a fog measuring section for measuring optical density of light reflected by said chemical analysis slide before said chemical analysis slide is provided with said substance to be measured is accommodated in said temperature-controlled chamber on the lateral side of said incubator, said read-out head is moveable to face said fog measuring section, and said chemical analysis slide is made to pass through said fog measuring section before said chemical analysis slide is provided with said substance to be measured, whereby fog measurement is carried out by said read-out head at said fog measuring section.

5. A chemical analysis apparatus provided iwth an incubator having at least one housing compartment for housing a chemical analysis slide having a reagent layer with a substance, which is to be measured, applied thereon, and for incubating the chemical analysis slide, and a read-out head disposed for standing face to face with the reagent layer of the chemical analysis slide housed in the housing compartment via a read-out opening formed in the housing compartment, thereby to emit measuring light to the reagent layer and to measure optical density of light reflected by the reagent layer, wherein the improvement comprises the provision of:

i) a temperature-controlled chamber for housing said incubator therein, ii) a first temperature adjustment means provided with a heater and a temperature sensor secured to said incubator, thereby to maintain the temperature in said housing compartment at a predetermined value, iii) a second temperature adjustment means provided with a heater and a temperature sensor disposed in said temperature-controlled chamber, thereby to maintain the temperature in said temperature-controlled chamber at said predetermined value, wherein said temperature-controlled chamber is supported in a main body of said chemical analysis apparatus via heat insulating materials, and said incubator is supported in said temperature-controlled chamber via heat insulating materials, and wherein a slide conveyance system for feeding said chemical analysis slide into said housing compartment is accommodated in said temperature-controlled chamber.

6. An apparatus as defined in claim 5 wherein a fog measuring section for measuring optical density of light reflected by said chemical analysis slide before said chemical analysis slide is provided with said substance to be measured is accommodated in said temperature-controlled chamber on the lateral side of said incubator, said read-out head is moveable to face said fog measuring section, and said chemical analysis slide is made to pass through said fog measuring section before said chemical analysis slide is provided with said substance to be measured, whereby fog measurement is carried out by said read-out head at said fog measuring section.

* * * * *